(12) United States Patent
Vacher et al.

(10) Patent No.: US 6,350,913 B1
(45) Date of Patent: Feb. 26, 2002

(54) 3-ALKOXYBENZYLAMINE DERIVATIVES AND THEIR USE AS MEDICINES FOR TREATING SCHIZOPHRENIA

(75) Inventors: Bernard Vacher; Stéphane Cuisiat, both of Castres; Wouter Koek, Viviers-les-Montagnes, all of (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/857,064
(22) PCT Filed: Dec. 1, 1999
(86) PCT No.: PCT/FR99/02981
     § 371 Date: May 29, 2001
     § 102(e) Date: May 29, 2001
(87) PCT Pub. No.: WO00/32557
     PCT Pub. Date: Jun. 8, 2000

(30) Foreign Application Priority Data

Dec. 2, 1998 (FR) .............................. 98 15207

(51) Int. Cl.$^7$ ..................... C07C 213/00; A61K 31/135
(52) U.S. Cl. .................. 564/354; 564/353; 564/347; 514/651
(58) Field of Search ................. 564/353, 354, 564/347; 514/651

(56) References Cited

FOREIGN PATENT DOCUMENTS

| EP | 0693474 | * | 1/1996 |
| EP | 0707007 | * | 4/1996 |
| FR | 2702211 | * | 9/1994 |
| WO | 9808817 | * | 3/1998 |

OTHER PUBLICATIONS

Menshaw et al: Bioorganic & Medicianal Chemistry Letters vol. 8, No. 3 pp. 295–300, Feb. 1998.*

* cited by examiner

Primary Examiner—Samuel Barts
(74) Attorney, Agent, or Firm—The Firm of Hueschen and Sage; G. Patrick Sage

(57) ABSTRACT

The present invention relates to novel 3-alkoxybenzylamine derivatives of general formula (1):

formula 1

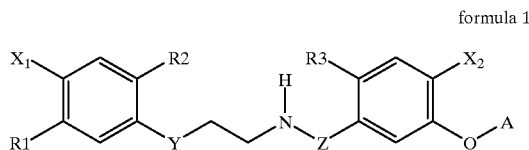

which are useful as medicinal products and in particular as antipsychotic agents.

9 Claims, No Drawings

3-ALKOXYBENZYLAMINE DERIVATIVES AND THEIR USE AS MEDICINES FOR TREATING SCHIZOPHRENIA

This is a 371 application of PCT/FR99/02981 filed Dec. 01, 1999.

Dopamine is a neuromnediator which is involved in controlling motricity, cognitive functions and moods, and is involved in the compensation circuit. Five types of dopaminergic receptor ($D_1$–$D_5$) have been cloned and their levels of expression and cerebral distributions have been analyzed. Among these five types of receptor, at least two types have isoforms (Proc. Natl. Acad. Sci. USA 1998, 95, 7731). Although pharmacologically different, these five types of dopaminergic receptor have been grouped into two subfamilies: the subfamily $D_1$, which comprises the $D_1$ and $D_5$ receptors, and the subfamily $D_2$ which comprises the $D_2$, $D_3$ and $D_4$ receptors. It is possible to differentiate the pharmacological action of the subfamilies $D_1$ and $D_2$, but it is generally difficult to differentiate the function of the various types within each subfamily.

A dysfunction of dopaminergic transmission is involved in the symptomatology of disorders of the central nervous system such as schizophrenic psychosis (Neuropsychopharmacol. 1988, 1, 179), certain neurodegenerative diseases such as, for example, Parkinson's disease (Neurodegenerative Diseases; Jolles, G.; Stutzmann, J. M.; Eds; Academic Press, 1994, Chap. 8), depression (J. Clin. Psychiatry, 1998, 59 (Suppl. 5), 60), and dependency on certain substances such as, for example, cocaine, tobacco or alcohol (Cell 1997, 90, 991; Nature 1997, 388, 586).

Thus, for example, antagonists of the $D_2$-type central dopaminergic receptors constitute a conventional and clinically effective approach towards treating the positive symptoms of schizophrenic psychosis. However, most of the compounds with such a mechanism of action also induce adverse side effects such as Parkinson-type symptoms (Pharmacotherapy 1996, 16, 160) and/or neuroendocrine disorders (Acta Psychiatr. Scand. 1989, 352, 24).

Mewshaw et al. (Bioorg. Med. Chem. Lett. 1998, 8, 295) have disclosed phenoxyethylamines of formula:

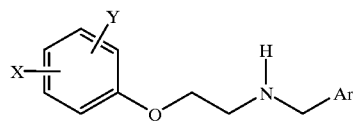

in which X represents a hydrogen atom, a hydroxyl group, an amino group or a methanesulfonamide group, Y represents a hydrogen atom or a halogen atom and Ar is a phenyl or 2-thienyl group, as being partial agonists of $D_2$-type receptors.

Patents WO 98/08817, U.S. Pat. No. 5,760,070, WO 98/08843 and WO 98/08819 respectively disclose 4-aminoethoxyindoles and 4-aminoethoxyindolones as being agonists of $D_2$-type dopaminergic receptors or inhibitors of dopamine synthesis and release.

Unangst et al. (J. Med. Chem. 1997, 40, 4026) have disclosed aryloxyalkylamines of formula:

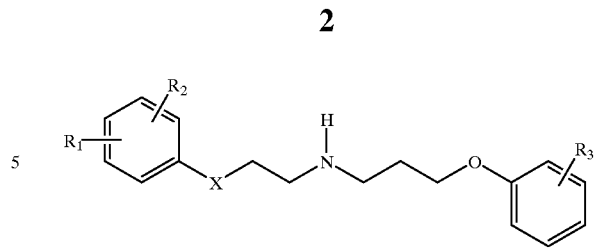

in which X represents an oxygen or sulfur atom or a $CH_2$ group; $R_1$ is a hydrogen or chlorine atom, a hydroxyl or hydroxymethyl group, a nitro group or a hydroxycarbonyl residue; $R_2$ and $R_3$ represent a hydrogen atom, a halogen atom or a methyl group. These compounds are active on the dopaminergic system, in particular on the $D_4$-type receptors, and are potentially useful for treating schizophrenia.

Patent WO 97/23482 discloses octahydropyrrolo[1,2-a] pyrazines of formula:

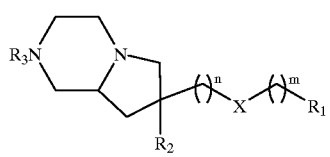

in which X represents, inter alia, a hydrogen atom; m and n=0, 1 or 2 and $R_1$ is an unsubstituted, heterocyclic or non-heterocyclic, polycyclic or non-polycyclic aromatic group. These compounds have affinity for dopaminergic receptors and in particular for the $D_4$-type receptors.

Patents FR 2 702 211, JP 51 048 627, JP 51 052 146, DE 2 450 616 and WO 96/31461 disclose 2-[2-(alkoxy) phenoxy]ethylamine derivatives of formula:

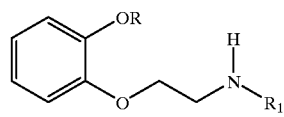

in which R is a $C_1$–$C_4$ alkyl group and $R_1$ represents a 4-benzenebutyl, 4-piperidinemethyl or 4-benzamidobutyl chain. These compounds are claimed as being ligands of the 5-$HT_{1A}$ sub-type receptors (FR 2 702 211 and WO 96/31461) or hypotensive agents and tranquilizers (JP 51 048 627, JP 51 052 146 and DE 2 450 616).

Patent EP 707 007 discloses arylamines with twofold activity simultaneously antagonist towards $D_2$-type receptors and agonist towards 5-$HT_{1A}$ sub-type receptors, which are useful as antipsychotic agents. The compound EMD-12830 (Drug Data Report 1998, 21) of formula:

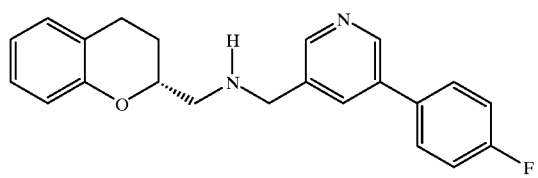

is claimed as an atypical antipsychotic agent (i.e. an agent with less of a propensity to induce Parkinson-type side effects than conventional antipsychotic agents).

Patent DE 2 364 685 discloses phenoxyalkylamines, in particular N-[2-(2-methoxyphenoxy)ethyl]pyrid-3- or 4-ylmethanamine are claimed as hypotensive agents.

Angstein et al. (J. Med. Chem. 1965, 8, 356) have disclosed aryloxyalkylamines which are active on the cardiovascular system. Among the compounds disclosed is N-[2-(2-methoxyphenoxy)ethyl]benzenemethanamine.

Goldenberg et al. (Chim. Ther. 1973, 8, 259) have disclosed, inter alia, N-[2-(2-methoxyphenoxy)ethyl-2-benzofuranmethanamines as agents with peripheral vasodilatatory properties.

4-Methoxy-3-[2-[(phenylmethyl)amino]ethoxy]phenol is disclosed in J. Labelled Compd. Radiopharm. 1993, 33, 1091 and N-[2-(2-methoxyphenoxy)ethyl]furfurylamine is disclosed in FR 1 336 684.

3-(Cyclopentyloxy)benzenemethanamine derivatives of formula:

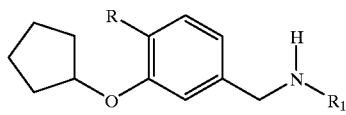

in which R represents a hydroxyl or methoxy group and $R_1$ represents an aromatic group or a substituted acyl or thioacyl group, are claimed as phosphodiesterase inhibitors in patents WO 97/46561, WO 95/20578, WO 95/04045, WO 94/02465 and WO 93/15044 or as active agents in the treatment of cardiac insufficiency in U.S. Pat. No. 4,971,959.

Patent WO 92/00968 discloses derivatives of formula:

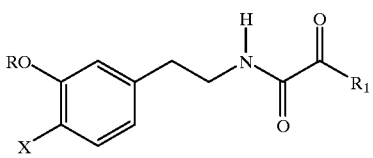

in which R represents a $C_4$–$C_6$ cycloalkyl group and X is a hydrogen, fluorine or chlorine atom, are claimed for their activity in controlling disorders dependent on TNF production.

Patent WO 98/01417 discloses aromatic and heteroaromatic compounds of formula:

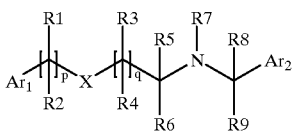

in which $Ar_2$ is, inter alia, an aromatic group optionally substituted with a non-cyclic lower alkoxy group. These compounds are claimed as influencing calcium receptors.

SUMMARY OF THE INVENTION

The present invention relates to a novel family of compounds which correspond to the general formula (1)

formula 1

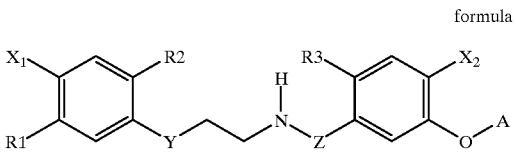

The compounds of this invention have antidopaminergic activity in particular on the receptors of the subfamily $D_2$. In this respect, the compounds of the invention are useful in the treatment of complaints resulting from dopaminergic hyperactivity, such as schizophrenic symptoms and dependency on certain substances. However, the antagonist activity of the products of the invention on the $D_2$-type receptors is exerted only during a transient dopaminergic hyperstimulation. In the absence of dopaminergic hyperactivity, i.e. when the dopamine concentration varies within proportions that are acceptable for normal functioning of neurones, the compounds of the invention do not induce a dopaminergic hyperactivity. The compounds of the invention are thus useful in the treatment of schizophrenic symptoms and have the advantage of being potentially free of the adverse side effects brought about by excessive blocking of the $D_2$-type receptors, such as Parkinson-type symptoms and/or endocrine disorders, at doses that are therapeutically effective for treating schizophrenic psychosis.

The compounds of the invention thus differ from the derivatives of the prior art in their chemical formula and their mechanism of action.

DETAILS OF THE INVENTION

More specifically, the present invention relates to novel compounds corresponding to the general formula (1):

formula 1

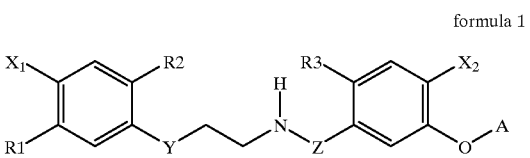

in which:

$X_1$ is a hydrogen, chlorine or fluorine atom;

$X_2$ has the same meaning as $X_1$;

$R_1$ represents:
   a hydrogen, chlorine or fluorine atom;
   a substituent $R_4$, a hydroxyl (OH) group, an alkoxy ($OR_4$) group, an alkylcarbonyloxy ($OC(O)R_4$) group, an alkylcarbonyl ($C(O)R_4$) group, an amino ($NH_2$) group, an alkylamino ($NHR_4$) group, a dialkylamino ($N(R_4)_2$) group, a [lacuna] ($NHC(O)R_4$) group or a cyano (CN) group;

$R_2$ is a substituent $R_4$ or an alkoxy ($OR_4$) group;

$R_3$ has the same meaning as $R_1$;

$R_4$ represents:
   a linear or branched $C_1$–$C_5$ alkyl radical optionally substituted with 1 or 2 fluorine atoms or a hydroxyl (OH) group and optionally containing a double bond;
   a 3-, 4-, 5- or 6-membered cycloalkyl radical optionally substituted with 1 or 2 fluorine atoms and optionally containing a double bond;

Y is an oxygen atom or a fluoromethylene (CHF) or difluoromethylene ($CF_2$) group;

z is a methylene ($CH_2$) group, optionally substituted with 1 or 2 methyl ($CH_3$) or fluoromethyl ($CH_2F$) groups;

A represents:
   a 3-, 4-, 5- or 6-membeed cycloalkyl radical or a 7- or 8-membered bicyclic radical optionally containing a double bond, an oxo (=O) function, a hydroxyl (OH) group, a methoxy ($OCH_3$) group or 1 or 2 fluorine atoms;
   a 5- or 6-membered non-aromatic heterocyclic group containing one or two hetero atoms chosen from nitrogen, oxygen and sulfur, optionally substituted with an oxo (=O) function, a hydroxyl (OH) group, a methoxy (OCH$_3$) group or 1 or 2 halogen atoms.

The invention also relates to the addition salts and optionally the hydrates of the addition salts of the compounds of general formula (1) with pharmaceutically acceptable mineral acids or organic acids.

A subject of the invention is also pharmaceutical compositions containing, as active principle, at least one of the derivatives of general formula (1) or one of the salts thereof or hydrates of the salts thereof in combination with one or more pharmaceutically acceptable excipients, adjuvants or vehicles. Examples which may be mentioned are inclusion complexes, in particular the inclusion complexes formed by the compounds of the invention with β-cyclodextrins.

The pharmaceutical compositions according to the invention are compositions which may be administered orally, nasally, sublingually, rectally or parenterally. It is generally advantageous to formulate such pharmaceutical compositions in unit dose form. In this case, each dose comprises a predetermined amount of the active principle, combined with the vehicle, excipients and/or adjuvants that are suitable, calculated to obtain a given therapeutic effect. As examples of unit dose forms which may be administered orally, mention may be made of tablets, gel capsules, granules, powders and oral solutions or suspensions.

The formulations that are suitable for the chosen administration form are known and described, for example, in: Remington, The Science and Practice of Pharmacy, 19$^{th}$ Edition, 1995, Mack Publishing Company and may thus be readily prepared by a person skilled in the art.

It is known that the dosage varies from one individual to another, according to the nature and severity of the complaint, the chosen route of administration and the weight, age and sex of the patient, and the effective doses will consequently have to be determined as a function of these parameters by a person specialized in the field. As a guide, the effective doses may range between 0.001 and 100 mg/kg/day.

The compounds of general formula (1) may exist in several tautomeric forms. Although not explicitly reported in the present patent application to simplify the graphical representation of the structural formulae, such tautomeric forms are nevertheless included in the field of application of the invention.

When the compounds of the invention comprise an asymmetric carbon atom, the invention relates both to the racemic mixtures and to the various enantiomers of the compound under consideration, and also to mixtures thereof in all proportions.

According to one specific characteristic of the present invention, R$_2$ represents an isopropoxy.

According to another specific characteristic of the present invention, Y represents an oxygen atom and Z represents a methylene group.

According to another particular characteristic of the present invention, A is chosen from cyclopentyl, cyclohexyl, 2-cyclohexenyl and bicyclo[2.2.1]hept-5-en-2-yl groups.

The compounds of general formula [lacuna] in which:
Y has the same meaning as above,
z represents a methylene radical optionally substituted with a methyl or fluoromethyl group,
X$_1$, X$_2$, R$_1$, R$_2$, R$_3$, R$_4$ and A have the same meaning as above, may be prepared according to the process described in Scheme A.

Scheme A

The compound of formula (1) is prepared by a conventional reductive amination reaction between the compound of formula (2), in which w represents a hydrogen atom or a methyl or fluoromethyl radical, and the primary amine of formula (3). The expression "a conventional reductive amination reaction" means that the compound of formula (2) and the amine (3) are reacted in the suitable solvent and that the mixture of reagents (2) and (3) is then subjected to the reducing agent according to a method that is well known to those skilled in the art.

The compounds of formula (1) are purified according to one or more methods chosen from crystallization and/or liquid-phase chromatography techniques. If so desired, they may then be:

salified using a pharmaceutically acceptable acid;
used in the formation of an inclusion complex.

The process for preparing the primary amines of formula (3) depends on the nature of the substituents X$_1$, R$_1$ and R$_2$ borne by the benzene nucleus.

The derivative of formula (4a), which is a precursor of the primary amine (3), in which:

X$_1$ is a hydrogen, chlorine or fluorine atom,
R$_1$ is a hydrogen or fluorine atom, a formnyl group, a nitro group or an ethoxycarbonyl (C(O)OEt) group,
may be obtained by the process described in Scheme B.

Scheme B

4-Nitrocatechol is regioselectivity alkylated using a 2-balopropane to give the derivative (5-3; R$_1$=NO$_2$) according to an experimental protocol similar to that described in (Org. Prep. Proced. Int. 1992, 23, 753). 2-Hydroxy-3-isopropoxybenzaldehyde (5-2; R$_1$=CHO) is a compound which is known in the chemical literature (Heterocycles 1984, 22 (9), 1995). The preparation of 2-isopropoxy-5-ethoxycarbonylphenol (5-1; R$_1$=CO$_2$Et) is disclosed in EP 579 223. A conventional Williamson reaction (J. Med. Chem. 1989, 32, 105) between the appropriate compounds of formula (5) and 1-bromo-2-chloroethane gives the corresponding chloro ether, which, by reaction with potassium phthalimide (Gabriel synthesis) gives the protected amines of formula (4a) in which R$_1$ is H, CHO, NO$_2$, CO$_2$Et and X$_1$ is a hydrogen atom. Under conditions similar to those used to convert the phenol of formula (5) into the protected amine of formula (4a), 5-fluoro-2-hydroxyacetophenone is converted into the protected amine of formula (7; R=CH$_2$CH$_2$NPht). A Bayer-Villiger reaction carried out on the compound of formula (7), Synth. Commun 1989, 11/12, 2001, followed by a basic hydrolysis reaction of the intermediate formate gives the phenol of formula (6; R=CH$_2$CH$_2$NPht). Alkylation of the phenol of formula (6) under the usual conditions gives the compound of formula (4a) in which R$_1$ is a fluorine or chlorine atom and X$_1$ is a hydrogen atom. Inversion of the order of incorporation of the alkyl residues on the intermediates of formulae (7) and (6) gives access, under experimental conditions identical to those described above, to the compounds of formula (4a) in which R$_1$ is a hydrogen atom and X$_1$ is a fluorine or chlorine atom.

The amine derivatives of formula (4b–f), which are precursors of the primary amiines (3), in which:

X$_1$ is a hydrogen atom,
R$_1$ is a group R$_4$, C(O)R$_4$, OH or OR$_4$,
may be obtained according to the process described in Scheme C.

Scheme C

The compound of formula (4a-2) is the intermediate used to prepare the protected arnines of formulae (4b–g).

According to route a: a conventional Wittig reaction between the intermediate of formula (4a-2) and methyltnphenylphosphonium iodide gives the vinyl derivative of formula (4b). The derivative of formula (4b) may:
- either be used directly in the preparation of the compounds of formula (1) in which $R_4$ is a vinyl group;
- or be reduced, under conventional hydrogenation conditions catalyzed with transition metals, to give the compound of formula (4c);
- or be oxidized, according to a conventional Wacker reaction (Org. Synth. 1988, 67, 12) to give the compound of formula (4d). A process similar to the process described by route a may then be repeated using the ketone (4d) to give the compound of formula (4e).

The use of a non-stabilized phosphonium ylid, derived from a higher alkane halide, gives access to the derivatives of formula (4b–e) in which $R_1$ represents a group $R_4$ or $C(O)R_4$ other than a methyl group.

The ketone function of the derivative of formula (4d) may also be reduced to a secondary alcohol function such as, for example, that present in compound 4h.

According to route b: a Bayer-Villiger reaction, under conditions identical to those described for the preparation of the phenol of formula (6) from the intermediate of formula (7), Scheme B, gives the phenol of formula (4f) which may then be alkylated, under the usual conditions, to give the derivatives of formula (4g).

The derivatives of formula (4i), which are precursors of the primary amines (3), in which:
- $X_1$ is a hydrogen atom,
- $R_1$ is a group $NH_2$, $NHR_4$, $N(R_4)_2$ or $NHC(O)R_4$, are obtained according to the process described in Scheme D.

Scheme D

The intermediate of formula (4a-6) is prepared by means of a Mitsunobu reaction between the compound of formula (5; $R_1=NO_2$, Scheme A) and tert-butyl (2-hydroxyethyl) carbamate (Eur. J. Med. Chem. 1995, 30, 387). Reduction of the nitro function of the compound of formula (4a-6), J. Org. Chem. 1987, 52, 1844, gives the amine of formula (4g-2). Acylation of the amine of formula (4g-2), under conventional experimental conditions, gives the derivative of formula (4i) in which $R_1$ is a group ($R_4CONH$). The derivatives of formula (4i) in which $R_1$ represents a group $NHR_4$ or $N(R_4)_2$ are readily prepared from the compound of formula (4g-2) by means of reactions that are well known to those skilled in the art.

The compounds of formula (4j) or (4k) in which:

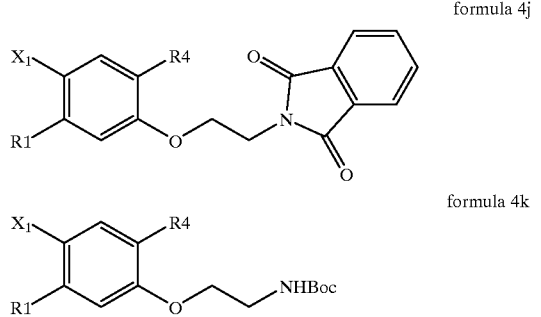

formula 4j formula 4k $X_1$, $R_1$ and $R_4$ have the same meaning as above, are prepared according to processes similar to those described for the preparation of the compounds of formula (4a–i) from suitably substituted phenols, which are commercially available or prepared according to methods known in the chemical literature.

The primary amines of formula (3), prepared by deprotection of the compounds of formula (4a–i), are used immediately in the following reductive amination step (Scheme A). The methods for deprotecting the amines of formulae (4a–i) are described in Scheme E.

Scheme E

Deprotection of the compounds of formula (4a–h) is carried out by moderate heating (60° C.) of the derivatives of formula (4a–h) in the presence of an excess of 2-aminoethanol (route a). Deprotection of the compounds of formula (4i) is carried out by treating a solution of compounds (4i) in dichloromethane with an excess of trifluoroacetic acid (route b).

The process for preparing the aldehydes of formula (2), Scheme A, depends on the nature of the substituent $R_3$.

The aldehydes of formula (2a) in which:
- $R_3$ is a hydrogen atom or an $OCH_3$ group,
- A has the same meaning as above, are prepared by the process described in Scheme F.

Scheme F

3-Hydroxybenzaldehyde or 2-methoxy-5-hydroxybenzaldehyde, prepared according to J. Org. Chem. 1974, 39, 2437, is alkylated using the appropriate cycloalkane halide or cycloalkene halide, under conditions that are identical to those described above for the formation of the ether of formula (5) from 4-nitrocatechol (Scheme B), to give the compounds of formula (2a) in which $R_3$ is a hydrogen atom or a methoxy group. However, when A represents a bicyclic group, for example a bicyclo[2.2.1]hept-5-ene group, the etherification reaction under consideration is preferably accomplished using the appropriate bicyclic alcohol by means of a Mitsunobu reaction according to a procedure which is identical to the one described in (J. Med. Chem. 1991, 34, 291).

The aldehydes of formulae (2b) in which:
- $R_3$ is a fluorine atom or a chlorine atom,
- A has the same meaning as above, are prepared by the process described in Scheme G.

Scheme G

The appropriate 3-methyl-4-halophenol ($R_3=Cl$ or F) is alkylated under conditions identical to those used for the preparation of the compound of formula (2a) from the corresponding phenol (Scheme F). The compound of formula (8) is then selectively brominated on the methyl group in the benzylic position (J. Med. Chem. 1982, 25, 1204) to give the compound of formula (9) which is oxidized to the aldehyde of formula (2b) according to the method developed by Kornblum (J. Org. Chem. 1986, 51, 1264).

The aldehydes of formula (2c) in which:
- $X_2$ is a fluorine or chlorine atom,
- A has the same meaning as above, may be prepared according to a method which is identical to the one disclosed in WO 92/00968.

The compounds of formulae (4a–i) and (2a–c) constitute the set of compounds of formulae (4) and (2).

Scheme A

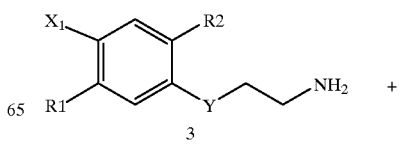

9
-continued
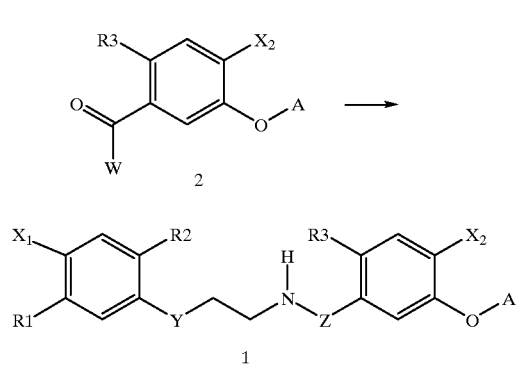
Scheme B
10
-continued
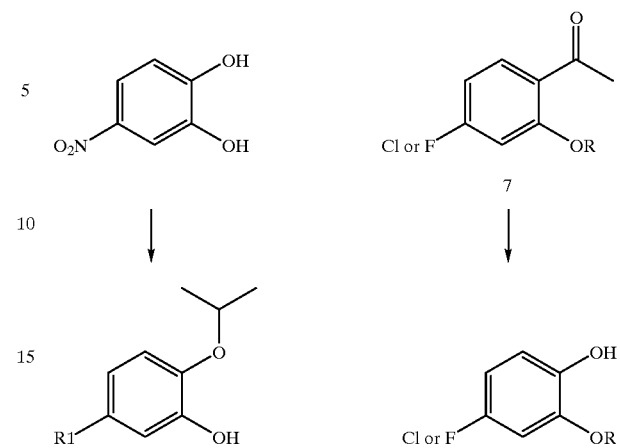
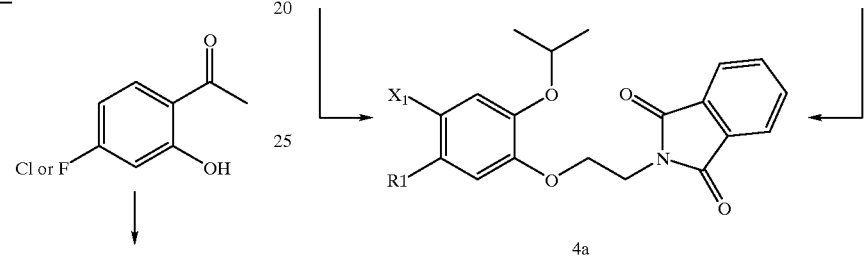
Scheme C
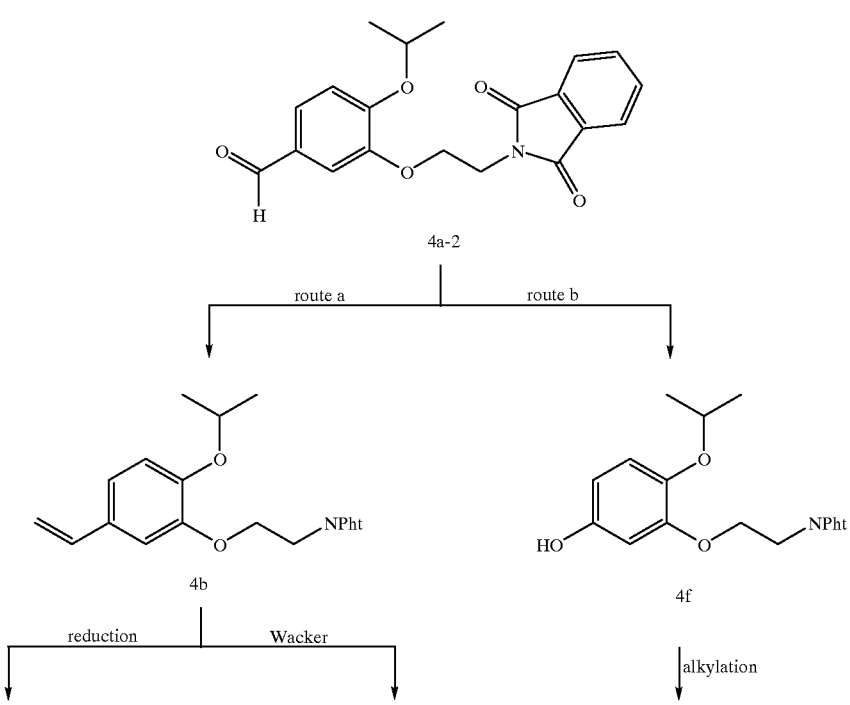

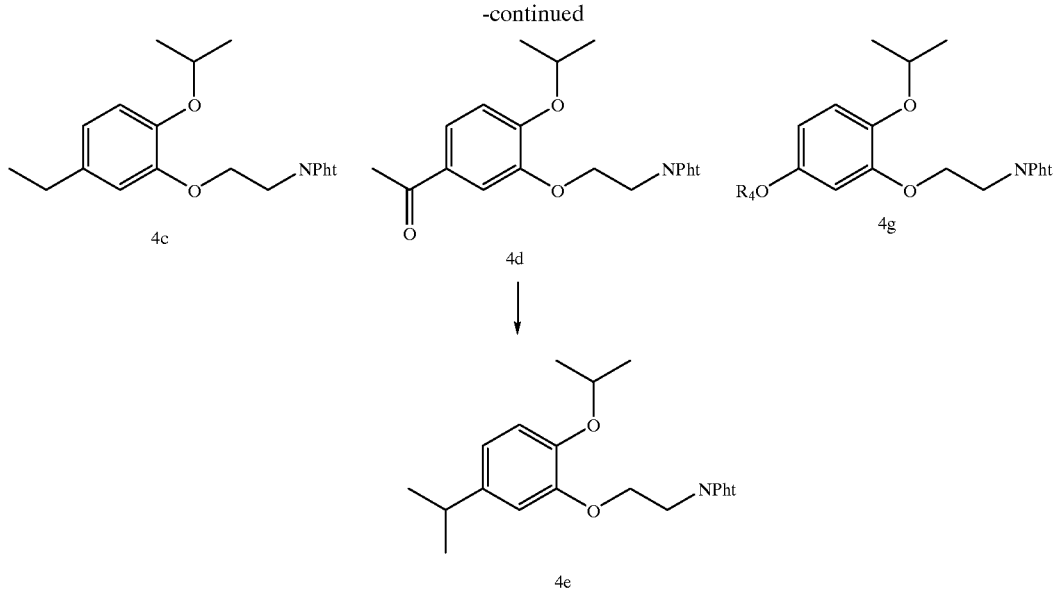
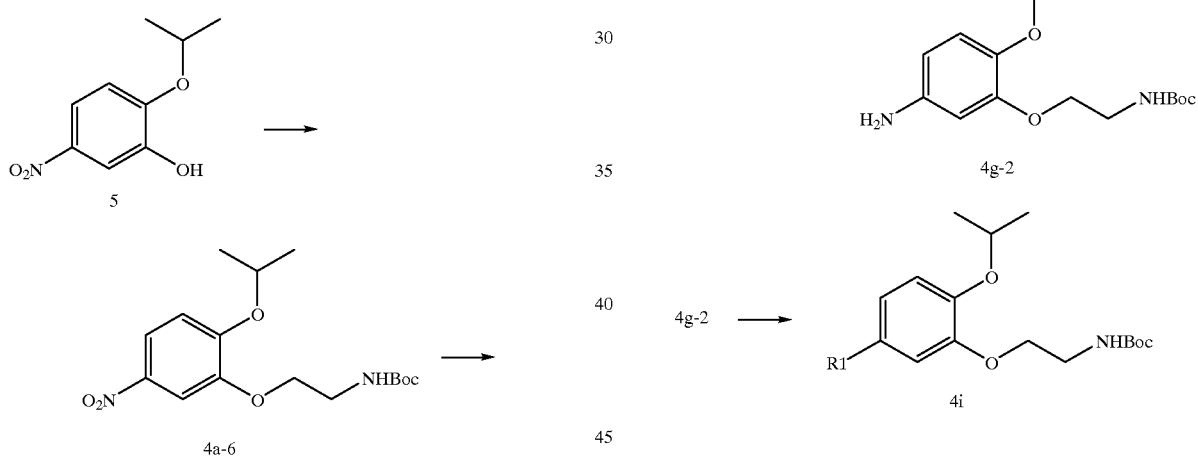
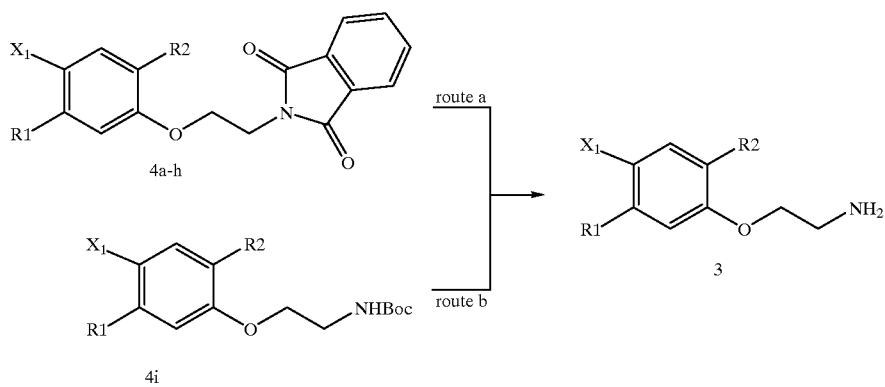

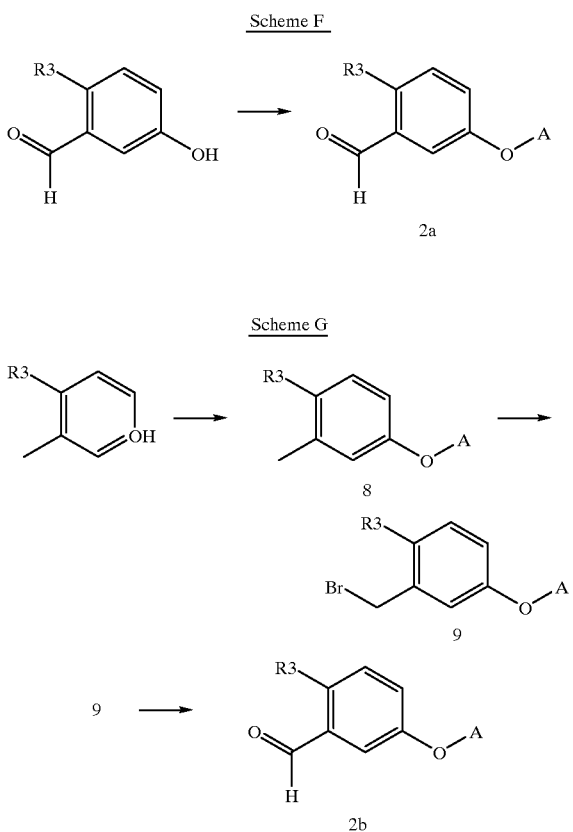

Scheme F

Scheme G

The examples which follow illustrate the invention without, however, limiting its scope.

In the examples below:
(i) The reaction progress is monitored by thin layer chromatography (TLC) and consequently the reaction times are mentioned only as a guide.
(ii) Different crystalline forms may give different melting points; the melting points reported in the present patent application are those of the products prepared according to the method described and are uncorrected.
(iii) The structure of the products obtained according to the invention is confirmed by the nuclear magnetic resonance (NMR) and infrared (IR) spectra and the elemental analysis, and the purity of the final products is checked by TLC.
(iv) The NMR spectra are recorded in the solvent indicated. The chemical shifts ($\delta$) are expressed in parts per million (ppm) relative to tetramethylsilane. The multiplicity of the signals is indicated by: s, singlet; d, doublet; t, triplet; q, quadruplet; m, multiplet; b, broad.
(v) The various symbols for the units have their usual meaning: mg (milligram); g (gram); ml (milliliter); ° C. (degrees Celsius); mmol (millimole); nmol (nanomole); cm (centimeter).
(vi) The abbreviations have the following meaning: m.p. (melting point); b.p. (boiling point).
(vii) In the present application, the pressures are given in millibar; the expression "room temperature" means a temperature of between 20° C. and 25° C.

EXAMPLE 1

2-Isopropoxy-5-nitrophenol (5)

A solution of 15.5 g of 4-nitrocatechol (100 mmol) in 200 ml of N,N-dimethylformamide is added dropwise at 0° C. to a 60% suspension of sodium hydride in oil (4.2 g, 105 mmol). At the end of the addition (1 hour), the dark red solution is stirred at 0° C. for 1.5 hours and 10.5 mnl of 2-iodopropane (105 mmol) are then added dropwise. The mixture is then brought to 80° C. and stirred for 16 hours. It is then cooled to room temperature, the solvent is evaporated off and the dark red oil is dissolved in dichloromethane (300 ml). The solution is washed with water and then with saturated aqueous sodium chloride solution, the organic phase is dried over sodium sulfate and filtered, and the solvent is evaporated off. The expected product is isolated by chromatography on a column of silica (eluent: 80/20 cyclohexane/ethyl acetate). 10.5 g of a yellow oil which solidifies are recovered:

Yield: 53%; m.p.: 139° C.; $^1$H NMR (DMSO d6) $\delta$: 1.31 (d, 6H); 4.76 (m, 1H); 7.24 (d, 1H); 7.63 (d, 1H); 7.76 (dd, 1H).

EXAMPLE 2

2-[2-(2-Acetyl-5-fluorophenoxy)ethyl]isoindole-1,3-dione (7)

Step 1: 1-[2-(2-chloroethoxy)-4-fluorophenyl]ethanone 40.5 ml of 1-bromo-2-chloroethane (490 mmol) are added to a solution of 25 g of 1-[2-hydroxy-4-fluorophenyl]ethanone (162 mmol) in 2-butanone (400 ml), followed by 45 g of potassium carbonate (320 mmol) and 1.26 g of potassium iodide (7.59 mmol).

The mixture is heated at 80° C. with vigorous stirring for 60 hours and is then cooled to room temperature and poured into ice-cold water. The resulting mixture is extracted with ethyl acetate and the organic phase is washed with saturated aqueous sodium chloride solution. The organic phase is then dried over magnesium sulfate and filtered, and the solvent is evaporated off. The product is crystallized from a cyclohexane/ethyl acetate mixture. 15.7 g of a white solid are recovered:

Yield: 45%; m.p.: 67° C.; $^1$H NMR (CDCl$_3$) $\delta$: 2.66 (s, 3H); 3.91 (t, 2H); 4.32 (t, 2H); 6.62 (dd, 1H); 6.76 (dt, 1H); 7.85 (dt, 1H).

Step 2: 2-[2-(2-acetyl-5-fluorophenoxy)ethyl]isoindole-1,3-dione

A mixture of 14.6 g of potassium phthalimide (79 mmol) and 15 g of 1-[2-(2-chloroethoxy)-4fluorophenyl]ethanone (69.2 mmol) in 150 ml of N,N-dimethyl-fornamide is heated at 150° C. for 6 hours. The mixture is then cooled and the solvent is evaporated off under vacuum. The solid obtained is taken up in dichloromethane and the organic phase is washed with water and then with saturated aqueous sodium chloride solution. The organic phase is then dried over magnesium sulfate and filtered, and the solvent is evaporated off. The product obtained is purified by crystallization from a cyclohexane/ethyl acetate mixture. 18.2 g of a white solid are obtained:

Yield: 76%; m.p.: 140° C.; $^1$H NMR (CDCl$_3$) $\delta$: 2.55 (s, 3H); 4.19 (t, 2H); 4.34 (t, 2H); 6.67 (m, 2H); 6.69 (m, 1H); 7.77 (m, 2H); 7.80 (m, 2H). IR (KBr) $\theta$: 1774, 1716, 1679, 1605 and 1590 cm$^{-1}$.

EXAMPLE 3

2-[2-(5-Fluoro-2-hydroxyphenoxy)ethyl]isoindole-1,3-dione (6)

A solution of 26 g of metachloroperbenzoic acid (at 55%, 82.9 mmol) in 220 ml of dichloromethane is stirred for one hour and then transferred into a separating funnel. The aqueous phase is separated out and the organic phase is placed in a round-bottomed flask and cooled to 0° C. 18 g of 2-[2-(2-acetyl-5-fluorophenoxy)ethyl]isoindole-1,3-dione (55 mmol) are added portionwise and the mixture is stirred at room temperature for 16 hours. 6.9 g of sodium bicarbonate (82 mmol) are then introduced portionwise and the mixture is stirred for one hour. The mixture is then concentrated under vacuum and 200 ml of methanol are added, followed by 15.2 g of potassium carbonate (110 mmol). The mixture is stirred for 4 hours at room temperature, the solvent is then evaporated off and replaced with 200 ml of dichloromethane, and the mixture is washed with water and with saturated aqueous sodium chloride solution. The aqueous phase is dried over sodium sulfate and filtered, and the solvent is evaporated off. The product is crystallized from dichloromethane. 14 g of the title product are obtained in the form of a white solid:

Yield: 84%; m.p.: 172° C.; $^1$H NMR (DMSO $d_6$) δ: 3.95 (t, 2H); 4.22 (t, 2H); 6.58 (dt, 1H); 6.75 (t, 1H); 6.85 (m, 1H); 7.64 (m, 4H); 8.77 (s, 1H (exchangeable)).

EXAMPLE 4

2-[2-(2-Isopropoxyphenoxy)ethyl]isoindole-1,3-dione (4a-1)

Working as in Example 2, but replacing the 1-[2-hydroxy-4-flourophenyl]ethanone with 2-isopropoxyphenol in Step 1:

Overall yield: 96%; m.p.: 72° C.; $^1$H NMR (CDCl$_3$) δ: 1.24 (d, 6H); 4.13 (t, 2H); 4.26 (t, 2H); 4.40 (m, 1H); 6.88 (m, 4H); 7.72 (m, 2H); 7.84 (m, 2H).

EXAMPLE 5

3-[2-(1,3-Dioxo-1,3-dihydroisoindol-2-yl)ethoxy]-4-isopropoxy-benzaldehyde (4a-2)

Working as in Example 2, but replacing the 1-[2-hydroxy-4-fluorophenyl]-ethanone with 3-hydroxy-4-isopropoxybenzaldehyde in Step 1, the title compound is prepared in the form of a white powder:

Overall yield: 95%; m.p.: 110° C.; Analysis $C_{20}H_{19}NO_5$; Calc %: C, 67.98; H, 5.42; N, 3.96; Found: 67.55; 5.30; 4.29; $^1$H NMR (CDCl$_3$) δ: 1.28 (d, 6H); 4.19 (t, 2H); 4.32 (t, 2H); 4.54 (m, 1H); 6.91 (d, 1H); 7.43 (m, 2H); 7.74 (m, 2H); 7.84 (m, 2H); 9.83 (s, 1H).

EXAMPLE 6

2-[2-(5-Nitro-2-isopropoxyphenoxy)ethyl]isoindole-1,3-dione (4a-3)

Working as in Example 2, but replacing the 1-[2-hydroxy-4-fluorophenyl]-ethanone with 2-isopropoxy-4-nitrophenol in Step 1, the title compound is prepared in the form of a yellow oil which crystallizes:

Overall yield: 85%; m.p.: 132° C.; $^1$H NMR (DMSO $d_6$) δ: 1.12 (d, 6H); 4.02 (t, 2H); 4.37 (t, 2H); 4.64 (m, 1H); 7.12 (d, 1H); 7.77 (d, 1H); 7.86 (m, 5H).

EXAMPLE 7

2-[2-(5-Fluoro2-isopropoxyphenoxy)ethyl]isoindole-1,3-dione 4a-4)

Working as in Example 1, but replacing the 2-isopropoxy-5-nitrophenol with 2-[2-(5-fluoro-2-bydroxyphenoxy)ethyl] isoindole-1,3-dione, the title compound is btained in the form of a white solid:

Yield: 77%; m.p.: 68° C.; $^1$H NMR (CDCl$_3$) δ: 1.20 (d, 6H); 4.14 (t, 2H); 4.23 (t, 2H); 4.30 (m, 1H); 6.56 (dt, 1H); 6.65 (dd, 1H); 6.79 (dd, 1H); 7.73 (m, 2H); 7.86 (m, 2H).

EXAMPLE 8

2-[2-(Isopropoxy-5-vinylphenoxy)ethyl]isoindole-1,3-dione (4b)

0.42 g of potassium tert-butoxide (3.75 mmol) is added portionwise to a suspension of 1.34 g of methyltriphenylphosphonium bromide (3.75 mmol) in 7.5 ml of tetrahydrofuran. The mixture is stirred for one hour at room temperature and is then cooled to 0° C. A solution of 1.20 g (3.4 mmol) of 3-[2-(1,3-dioxo-1,3-dihydroisoindol-2-yl) ethoxy]-4-isopropoxybenzaldehyde in 7 ml of tetrahydrofuran is then introduced. The mixture is then stirred at room temperature for 16 hours, after which it is poured into saturated aqueous ammonium chloride solution. This mixture is extracted with dichloromethane, the organic phase is washed with saturated aqueous sodium chloride solution, dried over magnesium sulfate and filtered, and the solvent is evaporated off under vacuum. The residue is purified by chromatography on a column of silica (eluent: 80/20 cyclohexane/ethyl acetate). 0.77 g of a yellow oil which crystallizes is obtained:

Yield: 64%; m.p.: 78° C.; $^1$H NMR (CDCl$_3$) δ: 1.25 (d, 6H); 4.14 (t, 2H); 4.28 (t, 2H); 4.42 (m, 1H); 5.13 (d, 1H); 5.58 (d, 1H); 6.63 (dd, 1H); 6.89 (d, 1H); 6.92 (dd, 1H); 7.01 (d, 1H); 7.73 (m, 2H); 7.84 (m, 2H).

EXAMPLE 9

2-[2-(5-Ethyl-2-isopropoxyphenoxy)ethyl]isoindole-1,3dione (4c)

0.15 g of 10% palladium-on-charcoal is added to a solution of 0.53 g of 2-[2-(isopropoxy-5-vinylphenoxy) ethyl]isoindole-1,3-dione (1.51 mmol) in 8 ml of methanol. The suspension is stirred under a hydrogen atmosphere for 2 hours, the solid is then removed by filtration on a silica filter, and the solvent is evaporated off. The title product is isolated by crystallization from a cyclohexane/ethyl acetate mixture. 0.53 g of a white solid is obtained:

Yield: 100%; m.p.: 61° C.; $^1$H NMR (CDCl$_3$) δ: 1.20 (t, 3H); 1.22 (d, 6H); 2.56 (q, 2H); 4.22 (t, 2H); 4.26 (t, 2H); 4.33 (m, 1H); 6.71 (dd, 1H); 6.76 (m, 2H); 7.74 (m, 2H); 7.83 (m, 2H).

EXAMPLE 10

2-[2-(5-Hydroxy-2-isopropoxyphenoxy)ethyl] isoindole-1,3-dione (4f)

Working as in Example 3, but replacing the 2-[2-(acetyl-5-fluorophenoxy)-ethyl]isoindole-1,3-dione with 3- [2-(1,3-dioxo- 1,3-dihydroisoindol-2-yl)ethoxy]-4-isopropoxybenzaldehyde, the title compound is obtained in the form of a white solid:

Yield: 65%; m.p.: 123° C.; $^1$H NMR (CDCl$_3$) δ: 1.20 (d, 6H); 4.14 (t, 2H); 4.26 (t, 2H); 4.68 (s, 1H (exchangeable)); 6.30 (dd, 1H); 6.46 (d, 1H); 6.74 (d, 1H); 7.73 (m, 2H); 7.85 (m, 2H); IR (KBr) v: 3252, 1711 and 1511 cm$^{-1}$.

EXAMPLE 11

2-[2-(2,5-Diisopropoxyphenoxy)ethyl]isoindole-1,3-dione (4g)

Working as in Example 7, but replacing the 2-[2-(5-fluoro-2-hydroxyphenoxy)-ethyl]isoindole-1,3-dione with 2-[2-(5-hydroxy-2-isopropoxyphenoxy)ethyl]isoindole-1,3-dione, the title compound is obtained in the form of a white solid:

m.p.: 66° C.; $^1$H NMR (CDCl$_3$) δ: 1.20 (d, 6H); 1.28 (d, 6H); 4.12 (t, 2H); 4.22 (t, 2H); 4.26 (m, 1H); 4.42 (m, 1H); 6.35 (dd, 1H); 6.50 (d, 1H); 6.76 (d, 1H); 7.72 (m, 2H); 7.85 (m, 2H).

EXAMPLE 12 tert-Butyl [2-(5-acetylamino-2-isopropoxyphenoxy) ethyl]-carbamate (4i)

The title compound is obtained in the form of an orange-colored oil:

Yield: 80%; $^1$H NMR (CDCl$_3$) δ: 1.33 (d, 6H); 1.45 (s, 9H); 2.15 (s, 3H); 3.46 (dt, 2H); 4.04 (t, 2H); 4.43 (m, 1H); 5.28 (s, 1H); 6.96 (d, 1H); 7.06 (d, 1H); 7.27 (dd, 1H).

EXAMPLE 13

3-(Bicyclo[2.2.1]hept-5-en-2-yloxy)benzaldehyde (2a-1)

3 g of bicyclo[2.2.1]hept-5-en-2-ol (27.2 mmol) and then 7.86 g of triphenylphosphine (30 mmol) are introduced at 0° C. into a solution of 3.66 g of 3-hydroxybenzaldehyde (30 mmol) in tetrahydrofuran (40 ml), and 13.6 ml of ethyl azodicarboxylate (40% in toluene, 30 mmol) are then added dropwise. The mixture is stirred at 75° C. for 48 hours, the solvent is then evaporated off, the residue is taken up in dichloromethane and the mixture is washed with normal aqueous sodium hydroxide solution, water and then saturated aqueous sodium chloride solution. The resulting solution is dried over magnesium sulfate, filtered and concentrated. The title product is isolated by chromatography on a column of silica (eluent: 88/12 cyclohexane/ethyl acetate). 0.6 g of a colorless oil is obtained:

Yield: 10%; $^1$H NMR (DMSO d$_6$) δ: 1.34 (m, 1H); 1.42 (m, 1H); 1.53 (m, 1H); 1.74 (m, 1H); 2.89 (s, 1H); 2.99 (s, 1H); 4.38 (d, 1H); 6.10 (m, 1H); 6.35 (m, 1H); 7.28 (m, 1H); 7.40 (s, 1H); 7.46 (m, 2H); 9.97 (s, 1H).

EXAMPLE 14

2-Methoxy-5-cyclopentyloxybenzaldehyde (2a-2)

5.45 g of potassium carbonate (39.4 mmol) and 4.2 ml of bromocyclopentane (39.4 mmol) are added to a solution of 4 g of 5-hydroxy-2-methoxybenzaldehyde (26.3 mmol) in 27 ml of acetonitrile. The mixture is stirred for 16 hours at 80° C. and is then poured into ice-cold water and extracted with ether, and the organic phase is washed with normal aqueous sodium hydroxide solution and then with saturated aqueous sodium chloride solution. The organic phase is dried over magnesium sulfate and filtered, and the solvent is evaporated off under vacuum. The title product is isolated by bulb-to-bulb oven distillation (T=200° C., P=10 mbar). 4.13 g of a pale yellow oil are obtained:

Yield: 71%; $^1$H NMR (CDCl$_3$) δ: 1.58–1.63 (m, 2H); 1.83–2.06 (m, 6H); 3.89 (s, 3H); 4.73 (m, 1H); 6.94 (d, 1H); 7.11 (dd, 1H); 7.28 (d, 1H); 10.40 (s, 1H).

EXAMPLE 15

5-Cyclopentyloxy-2-fluorobenzaldehyde (2b-1)
Step 1: 4-Cyclopentyloxy-1-fluoro-2-methylbenzene (8)
Working as in Example 14, but replacing the 5-hydroxy-2-methoxybenzaldehyde with 4-fluoro-3-methylphenol, the title product is obtained in the form of a pale yellow oil:

Yield: 75%; $^1$H NMR (CDCl$_3$) δ: 1.60 (m, 2H); 1.77–1.90 (m, 6H); 2.22 (s, 3H); 4.68 (m, 1H); 6.60 (m, 1H); 6.67 (m, 1H); 6.84 (t, 1H).

Step 2: 2-Bromomethyl-4-cyclopentyloxy-1-fluorobenzene (9)

4.81 g of N-bromosuccinimide (27 mmol) and 0.6 g of benzoyl peroxide (2 mmol) are introduced into a solution of 5 g of 4-cyclopentyloxy-1-fluoro-2-methylbenzene (25.8 mmol) in carbon tetrachloride (130 ml). The mixture is heated at 80° C. for 17 hours, a further 2.29 g of N-bromosuccinimide (12.89 mmol) and 0.3 g of benzoyl peroxide (1 mmol) are then added and heating is continued for 12 hours. The mixture is then cooled to room temperature and filtered through Celite. The mother liquor is concentrated and the black oil obtained is purified by chromatography on a column of silica (eluent: 88/12 cyclohexane/ethyl acetate). 4.63 g of an orange oil are obtained:

Yield: 66%; $^1$H NMR (CDCl$_3$) δ: 1.60 (m, 2H); 1.79–1.86 (m, 6H); 4.66 (m, 2H); 4.68 (m, 1H); 6.69 (d, 1H); 6.89 (t, 1H) 7.18 (d, 1H).

Step 3: 5-Cyclopentyloxy-2-fluorobenzaldehyde 1.9 ml of s-collidine (14.3 mmol) are introduced into a solution of 3 g of 2-bromomethyl-4-cyclopentyloxy-1-fluorobenzene (11 mmol) in 65 ml of dimethylsulfoxide. The mixture is heated at 150° C. for 25 minutes and is then cooled to room temperature. The solvent is evaporated off and the title product is isolated by chromatography on a column of silica (eluent: 96/4 cyclohexane/ethyl acetate). 1.1 g of a yellow oil are obtained:

Yield: 48%; $^1$H NMR (CDCl$_3$) δ: 1.61 (m, 2H); 1.68–1.72 (m, 4H); 1.88 (m, 2H); 4.33 (m, 1H); 7.24–7.32 (m, 3H); 10.16 (s, 1H).

EXAMPLE 16

(3–Cyclopentyloxybenzyl)[2-(2-isopropoxyphenoxy) ethyl]-amine (1–1)

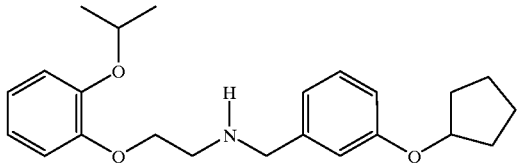

Step1: 2-(2-Isopropoxyphenoxy)ethylamine (3a-1)

1.10 g of 2-[2-(2-isopropoxyphenoxy)ethyl]isoindole-1,3-dione (3.38 mmol) are added to 4 ml of ethanolamine (66.3 mmol) and the solution is then maintained at 60° C. for 2 hours. The mixture is poured into ice-cold water and extracted with ethyl acetate. The organic phase is washed with saturated aqueous sodium chloride solution, dried over sodium sulfate and filtered and the solvent is evaporated off under vacuum. 0.66 g of the title product is obtained in the form of a pale yellow oil, which is used directly in the next step without further purification:

Yield: 100%; $^1$H NMR (DMSO d$_6$) δ: 1.24 (d, 6H); 1.46 (s, 2H (exchangeable)); 2.84 (t, 2H); 3.89 (t, 2H); 4.48 (m, 1H); 6.87 (m, 2H); 6.95 (m, 2H).

Step 2: (3-Cyclopentyloxybenzyl)[2-(2-isopropoxyphenoxy)ethyl]amine 0.5 g of 2-(2-isopropoxyphenoxy)ethylamine (2.56 mmol) and 0.49 [lacuna] of 3-cyclopentyloxybenzaldehyde (2.56 mmol) are mixed together in 20 ml of toluene. The solution is refluxed for 12 hours, while continuously removing the water formed. The toluene is then evaporated off, the residue is taken up in 20 ml of methanol and the solution is cooled to 0° C. 0.28 g of potassium borohydride (5.12 mmol) is added portionwise and the mixture is stirred for 3 hours at room temperature. The methanol is evaporated off, the residue is taken up in dichloromethane and the organic phase is washed with water and then with saturated aqueous sodium chloride solution. The organic phase is dried over magnesium sulfate and filtered, and the solvent is evaporated off under vacuum. The title product is isolated by chromatography on a column of silica (eluent: 98/1.5/0.5 dichloromethane/methanol/aqueous ammonia). 0.77 g of the title product is obtained in the form of a pale yellow oil:

Yield: 81%; $^1$H NMR (CDCl$_3$) δ: 1.31 (d, 6H); 1.60 (m, 2H); 1.77–1.92 (m, 4H); 2.07 (m, 2H); 3.03 (t, 2H); 3.85 (s, 2H); 4.13 (t, 2H); 4.47 (m, 1H); 4.76 (m, 1H); 6.75 (dd, 1H); 6.91 (m, 6H); 7.40 (t, 1H).

Preparation of the salt: 0.77 g of the title product (2.08 mmol) are dissolved in 10 ml of ethanol, followed by addition of 0.18 g of oxalic acid (2.08 mmol) in 10 ml of ethanol. The solution is concentrated, the salt precipitates and the concentrated solution is filtered. The salt is dried under vacuum at 50° C. 0.83 g of the title compound is obtained in the form of the oxalate, a white crystalline powder:

m.p.: 170° C.; Analysis C$_{25}$H$_{32}$NO$_7$; Calc %: C, 65.34; H, 7.24; N, 3.05 Found: 65.45; 7.29; 3.07; $^1$H NMR (DMSO d$_6$) δ: 1.24 (d, 6H); 1.58 (m, 2H); 1.69 (m, 4H); 1.92 (m, 2H); 3.26 (t, 2H); 4.24 (t, 2H); 4.26 (s, 2H); 4.55 (m, 1H); 4.81 (m, 1H); 6.87 –6.97 (m, 3H); 7.01–7.10 (m, 4H); 7.32 (t, 1H); IR (KBr) θ: 1612, 1686 and 2973 cm$^{-1}$.

The compounds of formula (1), obtained from the intermediates or from intermediates similar to those of Examples 1 to 15, according to a process similar to that of Example 16 and comprising the desired substituents, are collated in Table 1 below.

TABLE 1

| No. | X$_1$ | X$_2$ | R$_1$ | R$_2$ | R$_3$ | A | Salt | m.p.(° C.) |
|---|---|---|---|---|---|---|---|---|
| 1-2 | H | H | H | O-CH(CH$_3$)$_2$ | H | cyclohexyl | oxalate | 166 |
| 1-3 | H | H | H | O-CH(CH$_3$)$_2$ | H | cyclohexenyl | oxalate | 159 |
| 1-4 | H | H | H | O-CH(CH$_3$)$_2$ | H | norbornenyl | oxalate | 177 |
| 1-5 | H | H | F | O-CH(CH$_3$)$_2$ | H | cyclopentyl | oxalate | 170 |
| 1-6 | H | H | CH$_3$O | O-CH(CH$_3$)$_2$ | H | cyclopentyl | oxalate | 179 |
| 1-7 | H | H | (CH$_3$)$_2$CH-O | O-CH(CH$_3$)$_2$ | H | cyclopentyl | oxalate | 170 |
| 1-8 | H | H | CH$_2$=CH- | O-CH(CH$_3$)$_2$ | H | cyclopentyl | oxalate | 169 |
| 1-9 | H | H | CH$_3$CH$_2$- | O-CH(CH$_3$)$_2$ | H | cyclopentyl | oxalate | 169 |
| 1-10 | H | H | CH$_3$CO | O-CH(CH$_3$)$_2$ | H | cyclopentyl | oxalate | 183 |

TABLE 1-continued

| No. | X₁ | X₂ | R₁ | R₂ | R₃ | A | Salt | m.p.(° C.) |
|---|---|---|---|---|---|---|---|---|
| 1-11 | H | H | CH₃CONH |  | H | 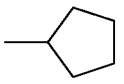 | oxalate | 169 |
| 1-12 | H | H | H |  | F | 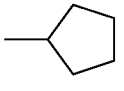 | oxalate | 159 |
| 1-13 | H | H | H |  | Cl | 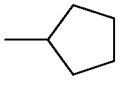 | oxalate | 110 |
| 1-14 | H | H | H |  | OCH₃ | 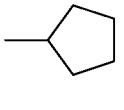 | oxalate | 132 |
| 1-15 | H | H | F |  | OCH₃ | 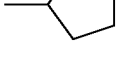 | oxalate | 140 |
| 1-16 | H | Cl | H |  | H | 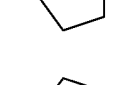 | oxalate | 118 |
| 1-17 | H | H | H |  | H |  | oxalate | 192 |
| 1-18 | H | H |  |  | H | 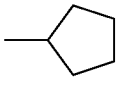 | oxalate | 175 |
| 1-19 | F | H | H |  | H | 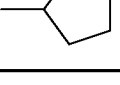 | oxalate | 170 |

Pharmacological Study of the Compounds of the Invention

1- Measurement of the affinity of the compounds of the invention for the $D_2$ receptors. The affinity of the compounds of the invention for the $D_2$-type receptors was determined by measuring the displacement of ($^3$H) YM-09151-2 (NET-1004 70-87 Ci/mmol), according to the method described in Naunyn-Schimiedeberg's Arch. Pharmacol. Methods, 1985, 329, 333. The pKi values (-log Ki) are given in the form of a mean±SEM of at least 3 experiments.

Table 2 gives, by way of example, the pKi values ($D_2$) for certain compounds of the invention in comparison with Risperidone.

2- Evaluation of the antagonist activity of the $D_2$ receptors and of the cataleptogenic effects of the compounds of the invention in vivo.

The test demonstrating the in vivo antidopaminergic activity of the compounds of the invention is based on the inhibition of behavioral patterns induced by methylphenidate, measured in rats, according to the method described in J. Pharmacol. Exp. Ther. 1993, 267, 181.

The test for evaluating the propensity of the products of the invention to induce side effects of extrapyramidal order is based on their cataleptogenic power, measured in rats, according to the method described in Eur. J. Pharmacol. 1996, 313, 25.

By way of example, the values obtained after i.p. administration are indicated in Table 2 in comparison with the reference substance: Risperidone.

TABLE 2

| Compound | $D_2$ pKi | Normalization ED₅₀ mg/kg | Catalepsy ED₅₀ mg/kg |
|---|---|---|---|
| 1.4 | 8.56 | 5.0 | >40 |
| 1.12 | 9.13 | 1.25 | >40 |
| Risperidone | 8.70 | 2.9 | 4.6 |

It emerges from this study that the compounds of the invention have high affinity for the $D_2$ type receptors and also powerful in vivo antidopaminergic activity. However, surprisingly, the compounds of the invention do not induce any cataleptogenic effects, or induced them only at very high doses, when compared with Risperidone. Risperidone is an atypical antipsychotic agent used clinically (Inpharma® 1998, 1156, 5).

In this respect, the compounds of the invention which are capable of modifying the effects of endogenous dopamine are useful in the treatment of dopaminergic disorders such as schizophrenia, certain neurodegenerative diseases and dependency on cocaine or alcohol or similar substances.

What is claimed is:

1. A compound selected from those of formula 1:

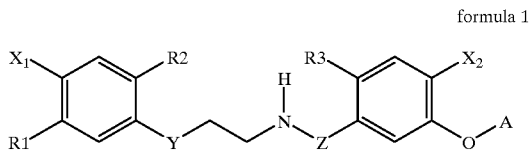

formula 1 in which:
$X_1$ is a hydrogen, chlorine or fluorine atom;
$X_2$ has the same meaning as $X_1$;
$R_1$ Represents:
  a hydrogen, chlorine or fluorine atom;
  a substituent $R_4$, a hydroxyl (OH) group, an alkoxy $(OR_4)$ group, an alkylcarbonyloxy $(OC(O)R_4)$ group, an alkylcarbonyl $(C(O)R_4)$ group, an amino $(NH_2)$ group, an alkylamino $(NHR_4)$ group, a dialkylamino $(N(R_4)_2)$ group, a $(NHC(O)R_4)$ group or a cyano (CN) group;
$R_2$ is a substituent $R_4$ or an alkoxy $(OR_4)$ group;
$R_3$ has the same meaning as $R_1$;
$R_4$ represents:
  a linear or branched $C_1$–$C_5$ alkyl radical optionally substituted with 1 or 2 fluorine atoms or a hydroxyl (OH) group and optionally containing a double bond;
  a 3-, 4-, 5-, or 6-membered cycloalkyl radical optionally substituted with 1 or 2 fluorine atoms and optionally containing a double bond;
Y is an oxygen atom or a fluoromethylene (CHF) or difluoromethylene $(CF_2)$ group;
Z is a methylene $(CH_2)$ group, optionally subsituted with 1 or 2 methyl $(CH_3)$ or fluoromethyl $(CH_2F)$ groups;
A represents:
  a 3-,4-,5- or 6-membered cycloalkyl radical or a 7- or 8-membered bicyclic radical optionally containing a double bond, an oxo (=O) function, a hydroxyl (OH) group, a methoxy $(OCH_3)$ group or 1 or 2 fluorine atoms;
  a 5- or 6-membered non-aromatic heterocyclic group containing one or two hetero atoms chosen from nitrogen, oxygen and sulfur, optionally substituted with an oxo (=O) function, a hydroxyl (OH) group, a methoxy $(OCH_3)$ group or 1 or 2 halogen atoms,
as well as the addition salt thereof with a pharmaceutically—acceptable mineral or organic acid and the hydrate of this salt, the compound possibly being in the form of a pure enantiomer or an enantiomeric mixture in all proportions, including a racemic mixture.

2. A compound of claim 1 wherein $R_2$ is isopropoxy.

3. A compound of claim 1 wherein:
Y represents an oxygen atom, and
Z represents a methylene group.

4. A compound of claim 1 wherein;
A is selected from cyclopentyl, cyclohexyl, 2-cyclohexenyl and bicyclo[2.2.1 ]hept-5-en-2-yl groups.

5. A compound of claim 1 selected from:
(3-Cyclopentyloxybenzyl)[2-(2-isopropoxyphenoxy) ethyl]amine,
(3-Cyclohexyloxybenzyl)[2-(2-isopropoxyphenoxy) ethyl]amine,
[3-(2-Cyclohexenyloxy)benzyl][2-(2-isopropoxyphenoxy)ethyl]amine,
[3-(Bicyclo[2.2.1]hept-5-en-2-yloxy)benzyl][2-(2-isopropoxyphenoxy)ethyllamine,
(3-Cyclopentyloxybenzyl)[2-(5-fluoro-2-isopropoxyphenoxy)ethyl]amine,
(3-Cyclopentyloxybenzyl)[2-(2-isopropoxy-5-methoxyphenoxy)ethyl]amine,
(3-Cyclopentyloxybenzyl)[2-(2,5-diisopropoxyphenoxy)ethyl]amine,
(3-Cyclopentyloxybenzyl)[2-(2-isopropoxy-5-vinylphenoxy)ethyl]amine,
(3-Cyclopentyloxybenzyl)[2-(2-isopropoxy-5-ethylphenoxy)ethyl]amine,
1-{3-[2-(3-Cyclopentyloxybenzylamino)ethoxy]-4-isopropoxyphenyl}ethanone,
N-{3-[2-(3-Cyclopentyloxybenzylamino)ethoxy]-4-isopropoxyphenyl}acetamide,
(5-Cyclopentyloxy-2-fluorobenzyl)[2-(2-isopropoxyphenoxy)ethyl]amine,
(2-Chloro-5-cyclopentyloxybenzyl)[2-(2-isopropoxyphenoxy)ethyl]amine,
(5-Cyclopentyloxy-2-methoxybenzyl)[2-(2-isopropoxyphenoxy)ethyl]amine,
(5-Cyclopenyloxy-2-methoxybenzyl)[2-(5-fluoro-2-isopropoxyphenoxy)ethyl]amine,
(4-Chloro-3-cyclopentyloxybenzyl)[2-(2-isopropoxyphenoxy)ethyl]amine,
(3-Cyclopentyloxybenzyl)]2-(4-fluoro-2-isopropoxyphenoxy)ethyl]amine,
(3-Cyclopentyloxybenzyl)[2-(2-isopropylphenoxy)ethyl] amine, and
1{3-[2-(3-Cyclopentyloxybenzylamino)ethoxy]-4-isopropoxyphenyl}ethanol.

6. A pharmaceutical compositioin comprising as active principle an effective amount of a compound of claim 1 together with one or more pharmacuetically—acceptable excipients or vehicles.

7. A method-of-treating an animal or human living body afflicted with schizophrenia comprising the step of administering to the living body an amount of a compound of claim 1 which is effective for alleviation of schizophrenia.

8. A method-of-treating an animal or human living body afflicted with dependency comprising the step of administering to the living body an amount of a compound of claim 1 which is effective for alleviation of dependency.

9. A method-of-treating an animal or human living body afflicted with neurodegenerative diseases comprising the step of administering to the living body an amount of a compound of claim 1 which is effective for alleviation of neurodegenerative diseases.

* * * * *

UNITED STATES PATENT AND TRADEMARK OFFICE
CERTIFICATE OF CORRECTION

PATENT NO. : 6,350,913
DATED : February 26, 2002
INVENTOR(S) : Bernard, Vacher et al.

It is certified that error appears in the above-identified patent and that said Letters Patent is hereby corrected as shown below:

Column 24,
Line 3, "bicyclo[2.2.1 ]" should read -- bicyclo[2.2.1] --.
Line 13, "ethyllamine," should read -- ethyl]amine, --

Signed and Sealed this

Twenty-first Day of May, 2002

*Attest:*

*Attesting Officer*

JAMES E. ROGAN
*Director of the United States Patent and Trademark Office*